United States Patent
Damania et al.

(10) Patent No.: US 10,856,741 B2
(45) Date of Patent: Dec. 8, 2020

(54) CORE BODY TEMPERATURE DETECTION DEVICE

(71) Applicant: Vital Connect, Inc., Campbell, CA (US)

(72) Inventors: Dhwanil Damania, Campbell, CA (US); Olivier Colliou, Los Gatos, CA (US); Arshan Aga, Mountain View, CA (US)

(73) Assignee: Vital Connect, Inc., San Jose, CA (US)

( * ) Notice: Subject to any disclaimer, the term of this patent is extended or adjusted under 35 U.S.C. 154(b) by 91 days.

(21) Appl. No.: 15/378,814

(22) Filed: Dec. 14, 2016

(65) Prior Publication Data

US 2018/0160909 A1    Jun. 14, 2018

(51) Int. Cl.
| | |
|---|---|
| *A61B 5/01* | (2006.01) |
| *A61B 5/00* | (2006.01) |
| *G01K 1/02* | (2006.01) |
| *G01K 13/00* | (2006.01) |
| *G01K 1/16* | (2006.01) |

(52) U.S. Cl.
CPC .............. *A61B 5/01* (2013.01); *A61B 5/6833* (2013.01); *G01K 1/024* (2013.01); *G01K 1/165* (2013.01); *G01K 13/002* (2013.01); *A61B 5/0008* (2013.01); *A61B 5/721* (2013.01); *A61B 2560/0412* (2013.01); *A61B 2562/043* (2013.01)

(58) Field of Classification Search
CPC ......... A61B 5/01; A61B 5/6833; A61B 5/721; A61B 2562/0271
See application file for complete search history.

(56) References Cited

U.S. PATENT DOCUMENTS

| | | | | |
|---|---|---|---|---|
| 3,933,045 A | * | 1/1976 | Fox .......................... | G01K 1/16 374/134 |
| 2004/0133081 A1 | * | 7/2004 | Teller ...................... | A61B 5/01 600/300 |
| 2007/0206655 A1 | * | 9/2007 | Haslett .................... | A61B 5/01 374/141 |
| 2007/0295713 A1 | * | 12/2007 | Carlton-Foss ........... | A61B 5/01 219/497 |
| 2008/0071189 A1 | * | 3/2008 | Yarden ..................... | A61B 5/01 600/549 |
| 2008/0170600 A1 | * | 7/2008 | Sattler ..................... | G01K 1/16 374/163 |
| 2008/0200969 A1 | * | 8/2008 | Weber ................. | A61B 18/1815 607/102 |
| 2008/0300819 A1 | * | 12/2008 | Koch ....................... | G01K 1/16 702/131 |
| 2009/0187115 A1 | * | 7/2009 | Yarden ..................... | A61B 5/01 600/549 |

(Continued)

FOREIGN PATENT DOCUMENTS

JP    2013210325 A  * 10/2013 ............. G01K 7/427

*Primary Examiner* — Sean P Dougherty
(74) *Attorney, Agent, or Firm* — Brundidge & Stanger, P.C.

(57) ABSTRACT

A system and method for detecting and monitoring core body temperature are disclosed. The system includes a patch device and an electronic module coupled to the patch device. The method includes providing a patch device, coupling an electronic module to the patch device to provide a wearable device, and monitoring core body temperature of a user using the wearable device.

20 Claims, 3 Drawing Sheets

(56) References Cited

U.S. PATENT DOCUMENTS

| | | | | |
|---|---|---|---|---|
| 2009/0234200 A1* | 9/2009 | Husheer | A61B 5/0008 | 600/301 |
| 2009/0306536 A1* | 12/2009 | Ranganathan | A61B 5/6804 | 600/549 |
| 2010/0121217 A1* | 5/2010 | Padiy | G01K 13/002 | 600/549 |
| 2010/0268113 A1* | 10/2010 | Bieberich | G01K 1/16 | 600/549 |
| 2010/0268114 A1* | 10/2010 | Van Duren | A61B 5/01 | 600/549 |
| 2010/0292605 A1* | 11/2010 | Grassl | G01K 1/165 | 600/549 |
| 2011/0051776 A1* | 3/2011 | Bieberich | G01K 1/165 | 374/163 |
| 2011/0133939 A1* | 6/2011 | Ranganathan | A61B 5/6833 | 340/584 |
| 2011/0213559 A1* | 9/2011 | Pollack | A61B 5/0008 | 702/19 |
| 2011/0249699 A1* | 10/2011 | Bieberich | G01K 1/165 | 374/1 |
| 2011/0249701 A1* | 10/2011 | Bieberich | G01K 13/002 | 374/163 |
| 2011/0264001 A1* | 10/2011 | Cheung | G01K 7/21 | 600/549 |
| 2011/0301493 A1* | 12/2011 | Husheer | G01K 7/42 | 600/549 |
| 2011/0317737 A1* | 12/2011 | Klewer | G01K 1/16 | 374/29 |
| 2012/0024833 A1* | 2/2012 | Klewer | G01K 1/14 | 219/211 |
| 2012/0109571 A1* | 5/2012 | Shimizu | G01K 1/165 | 702/130 |
| 2012/0109572 A1* | 5/2012 | Shimizu | G01K 13/002 | 702/131 |
| 2012/0238901 A1* | 9/2012 | Augustine | A61B 5/01 | 600/549 |
| 2012/0289855 A1* | 11/2012 | Bieberich | G01K 1/165 | 600/549 |
| 2013/0085708 A1* | 4/2013 | Sattler | G01K 1/20 | 702/131 |
| 2013/0151192 A1* | 6/2013 | Gilad-Bachrach | G01K 13/002 | 702/133 |
| 2013/0317388 A1* | 11/2013 | Bieberich | G01K 17/00 | 600/549 |
| 2013/0331728 A1* | 12/2013 | Sun | G01K 13/002 | 600/549 |
| 2014/0278201 A1* | 9/2014 | Shimizu | G01K 13/002 | 702/131 |
| 2015/0071325 A1* | 3/2015 | Kuroyama | G01K 13/002 | 374/134 |
| 2015/0160079 A1* | 6/2015 | Yarden | G01K 13/002 | 702/136 |
| 2016/0069752 A1* | 3/2016 | Shimizu | G01K 7/427 | 600/549 |
| 2016/0171363 A1* | 6/2016 | Mei | G06K 19/07773 | 235/492 |
| 2016/0183794 A1* | 6/2016 | Gannon | A61B 5/0008 | 600/549 |
| 2016/0302674 A1* | 10/2016 | Moyer | A61B 5/02055 | |
| 2017/0049397 A1* | 2/2017 | Sun | A61B 5/01 | |
| 2018/0008149 A1* | 1/2018 | Pekander | G01K 7/427 | |
| 2018/0160909 A1* | 6/2018 | Damania | A61B 5/01 | |
| 2018/0356298 A1* | 12/2018 | Atallah | G01K 1/165 | |

\* cited by examiner

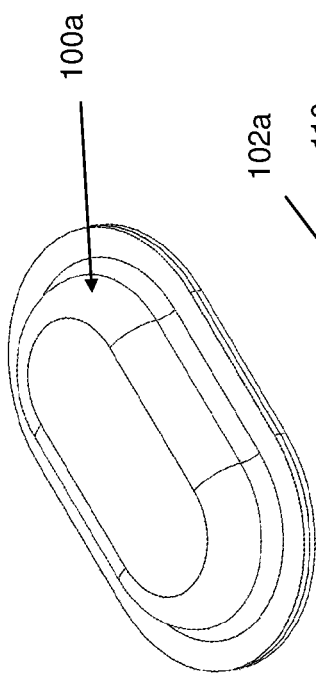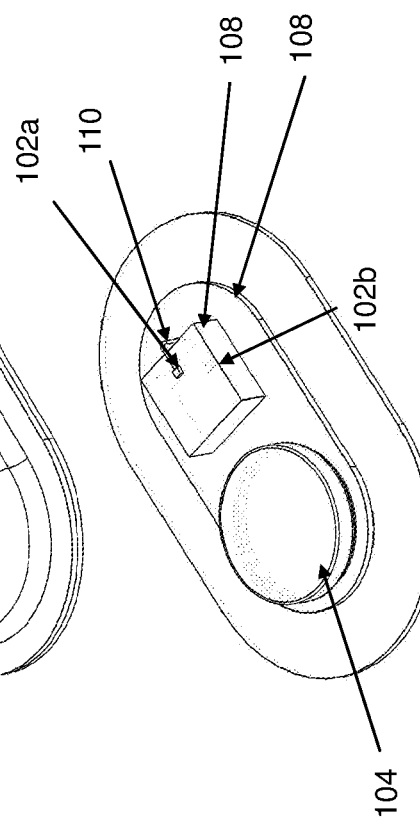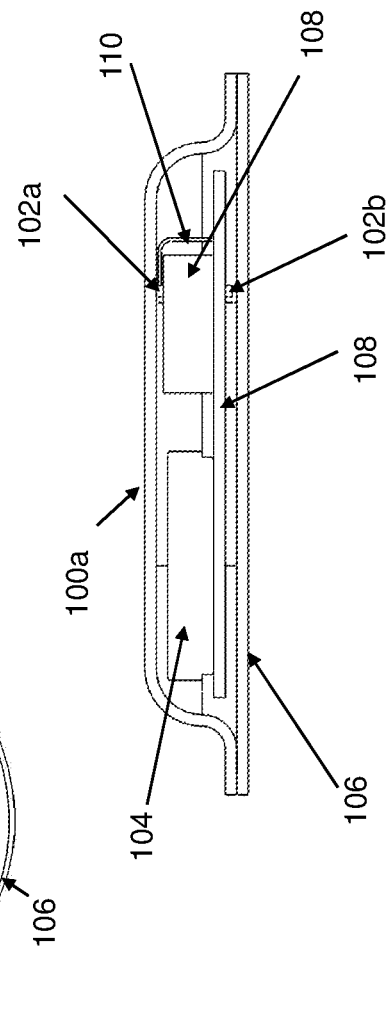

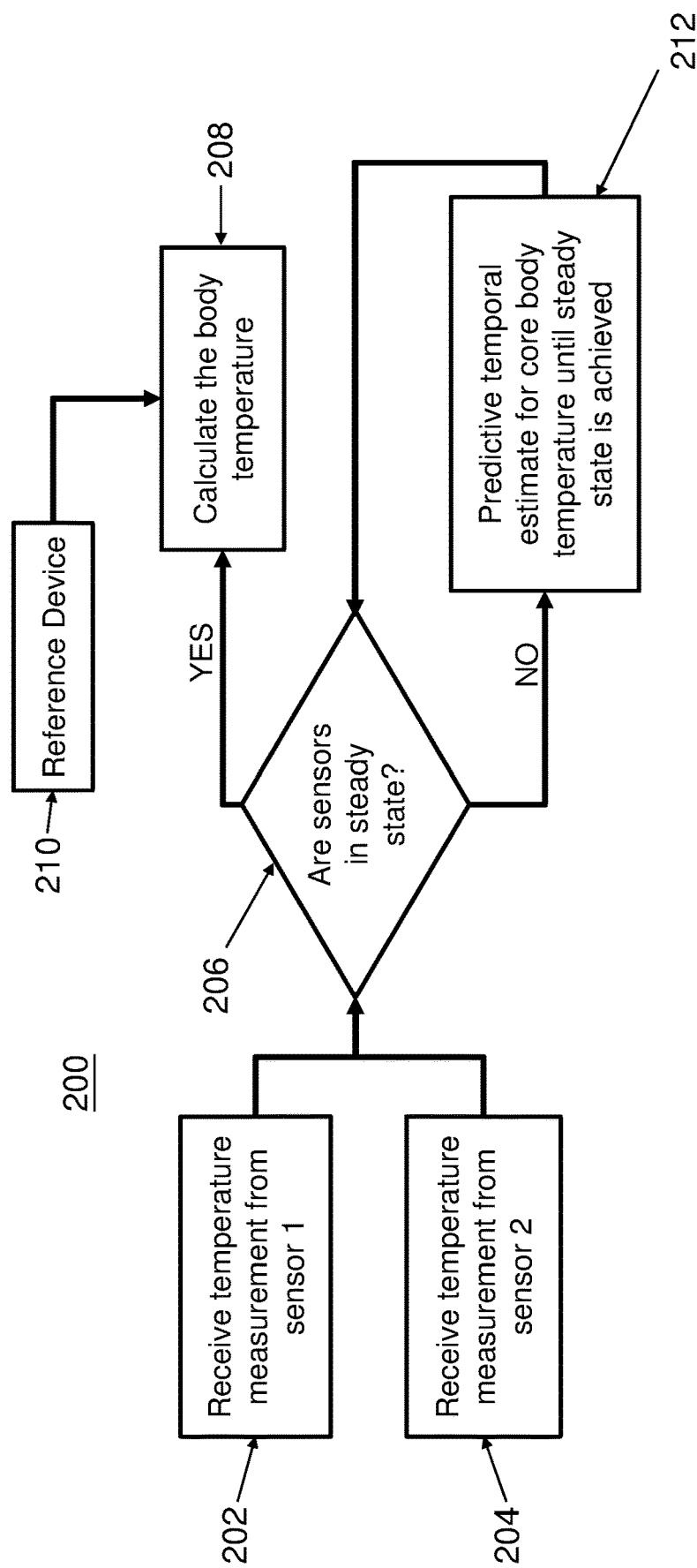

CORE BODY TEMPERATURE DETECTION DEVICE

FIELD OF THE INVENTION

The present invention relates to wearable sensor devices, and more particularly, to a wearable sensor device that detects core body temperature.

BACKGROUND

Human body (core) temperature is a clinically significant vital sign and must be monitored to ensure safe and effective care. It is maintained at a specific level by body's thermal regulation and can range between 35.5 and 41° C. Core body temperatures lower or higher than this range are possible in certain extreme situations. Typically, a core body temperature between 36.5-37.5° C. is considered normal, where a temperature greater than 37.5° C. is considered fever or hyperthermia dependent on the underlying mechanism resulting into increase and a temperature less than 35° C. is considered hypothermia. Critically, the body loses its thermal regulation outside the range of 35.5 to 41° C. and the survival of a human being is considered severely compromised.

Conventionally, there have been many attempts to non-invasively measure this clinically significant vital sign, but such methods have proven to be unsatisfactory for various reasons. For example, conventional methods face issues as being inadequately accurate and non-continuous. What is desired is continuous and sufficiently accurate detection and monitoring of core body temperature.

Therefore, there is a strong need for a solution that overcomes the aforementioned issues. The present invention addresses such a need.

SUMMARY OF THE INVENTION

A system and method for detecting and monitoring core body temperature are disclosed. In a first aspect, the system includes a patch device and an electronic module coupled to the patch device.

In a second aspect, the method includes providing a patch device, coupling an electronic module to the patch device to provide a wearable device, and monitoring core body temperature of a user using the wearable device.

BRIEF DESCRIPTION OF THE DRAWINGS

The accompanying figures illustrate several embodiments of the invention and, together with the description, serve to explain the principles of the invention. One of ordinary skills in the art readily recognizes that the embodiments illustrated in the figures are merely exemplary, and are not intended to limit the scope of the present invention.

FIG. 1A illustrates a wireless sensor device for detecting and monitoring core body temperature in accordance with an embodiment described herein.

FIG. 1B illustrates an isometric view of a wireless sensor device for detecting and monitoring core body temperature similar to FIG. 1A but with a top cover of the wireless sensor device removed, in accordance with an embodiment described herein.

FIG. 1C illustrates a cross-section view of wireless sensor device for detecting and monitoring core body temperature in accordance with an embodiment described herein.

FIG. 2 illustrates a method for monitoring core body temperature in accordance with an embodiment described herein.

DETAILED DESCRIPTION

Figure 3:
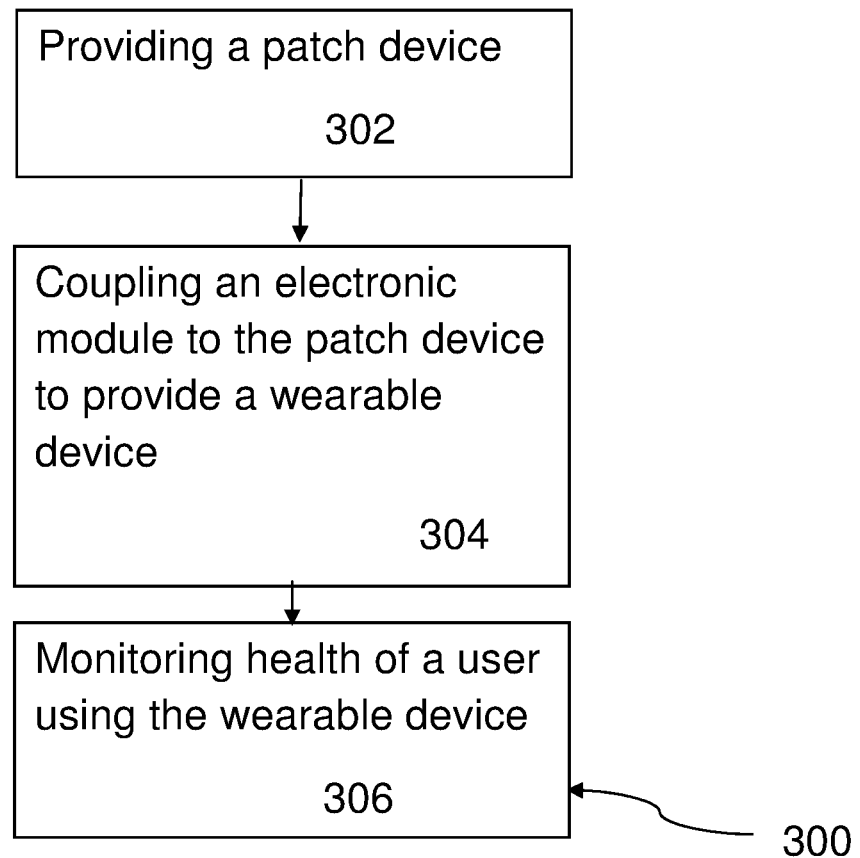
FIG. 3 illustrates another method for monitoring core body temperature in accordance with an embodiment described herein.

The present invention relates to wearable sensor devices, and more particularly, to a core body temperature detection device. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Wireless and wearable sensor devices can be utilized for the remote, automated, and continuous health monitoring of users/patients. A method and system in accordance with the present invention provides a wireless, portable, and wearable sensor device ("wearable device") that comprises a core body temperature detection component that is in a patch form factor and electronic modules coupled/attached to the core body temperature detection device. In another embodiment, the wearable device comprises one core body temperature detection component that includes two or more temperature sensors (e.g. thermistors, thermopiles etc.) separated by an insulating material (e.g. air, foam). The wearable device is attached to a user to automatically and continuously detect and monitor core body temperature.

In one embodiment, the core body temperature detection component of the wearable device is an ultra-low cost, and optionally fully disposable patch that is attached to the user's skin and used in conjunction with the electronic modules to detect, record, and analyze core body temperature.

In this embodiment, the wearable device capture temperature measurements using a plurality of sensors that include temperature sensors (e.g. thermistors, thermopiles etc.) separated by an insulating material (e.g. air, foam). The captured measurements are then processed and analyzed using either integrated processors and algorithms of the wearable device (e.g. the reusable electronic module, non-reusable electronic module) or an external processing device (e.g. smartphone device, cloud-based server network) to determine core body temperature.

To describe the features of the present invention in more detail, refer now to the following description in conjunction with the accompanying Figures.

FIG. 1 illustrates a wireless sensor device 100 for detecting core body temperature in accordance with an embodiment. As shown in FIG. 1, wireless sensor device 100 includes a top cover 100a, two sensors (that is, sensor 102a and sensor 102b), battery 104, a bottom layer 106, a plurality of spacers 108 and a sensor connector 110. While not shown in FIG. 1, further embodiments of wireless sensor device 100 include a processor coupled to sensors 102a and 102b via sensor connector 110, a memory coupled to the processor, an application coupled to the memory, and a transmitter coupled to the application.

In one embodiment, the wireless sensor device 100 is attached to a user to detect core body temperature via the sensors 102*a* and 102*b*. According to such an embodiment, bottom layer 106 includes a skin-friendly adhesive. According to one embodiment described herein, sensors 102*a* and 102*b* are temperature sensors (e.g. thermistors, thermopiles, etc.) separated by an insulating material. Although two sensors are shown in FIG. 1, additional embodiments disclosed herein may incorporate additional sensors. Furthermore, according to embodiments herein, additional sensors improve the accuracy of wireless sensor device 100 and the estimation of core body temperature. According to the embodiment of FIG. 1, the spacers 108 include a suitable insulating material and are utilized to separate sensors 102*a* and 102*b*. According to other embodiments not shown in FIG. 1, the insulating material separating sensors 102*a* and 102*b* are distinguishable from spacers 108. According to such embodiments, the insulating material separating sensors 102*a* and 102*b* may include air, foam and/or Polyetheretherketone (PEEK) for insulation. Furthermore, spacers 108 may include a printed circuit board or flex material. Other embodiments disclosed herein may also include any insulating material, so long as there is sufficient insulation between the temperature sensors to permit distinguishable temperature measurements from the sensors.

As explained in further detail below, sensor 102*a* and 102*b* obtain data from the user, where the process to obtain data includes any combination of analog, digital or algorithmic processes. After sensor 102*a* and 102*b* collect data from the user, the obtained data is transmitted to a memory (not shown in FIG. 1). Additionally, further embodiments disclosed herein further include an application that processes the obtained data via a processor (not shown in FIG. 1). According to one such embodiment, the processor executes the application to process and obtain information regarding the user's health. Moreover, in further embodiments, the processed information is transmitted to a transmitter and may, in turn, be relayed to another user or device for further processing, analysis, and storage (not shown in FIG. 1). In yet another embodiment, the transmitter transmits the various detected physiological signals in raw form to a remote device/server (e.g. smartphone, cloud-based server) for processing, analysis, and storage (not shown in FIG. 1).

Additionally, one of ordinary skill in the art readily recognizes that a variety of wireless sensor devices can be utilized in addition to the core body temperature detection device described above, including but not limited to, wearable devices, a wireless sensor device in a patch form-factor, tri-axial accelerometers, uni-axial accelerometers, bi-axial accelerometers, gyroscopes, and pressure sensors and that would be within the spirit and scope of the present invention.

FIG. 2 illustrates method 200 for monitoring core body temperature in accordance with an embodiment. As shown in FIG. 2, method 200 includes receiving a temperature measurement from sensor 1 (e.g., sensor 102*a* shown in FIGS. 1B and 1C) at step 202 and receiving a temperature measurement from sensor 2 (e.g., sensor 102*b* shown in FIGS. 1B and 1C) at step 204. Next, according to step 206, method 200 shown in FIG. 2 determines whether the sensors (e.g., sensor 102*a* and 102*b* shown in FIGS. 1B and 1C) are in a steady state. Accordingly, when the sensors are in a steady state, method 200 shown in FIG. 2 continues to step 208 and calculates the body temperature. Step 208 optionally receives, as one-time input, calibration data from a reference device at step 210. According to one embodiment, the reference device used at step 210 includes a standardized clinical thermometer. Moreover, according to one embodiment, the calibration performed at step 210 is performed one-time. In another embodiment, the calibration is performed at step 210 more than once to maintain a given accuracy. According to other embodiments, for example, when a reference device is not available, embodiments of the claimed invention include an adaptive correction factor to improve the accuracy of the estimates by removing the dependency on calibration. For example, embodiments of the adaptive correction factor depend on demographics, surround temperature range and relative change in different temperature data-streams. Embodiments described herein are not so limited, and one of ordinary skill in the art will readily recognize that there could be variations to the adaptive correction factor and those variations would be within the spirit and scope of the present invention.

On the other hand, if step 206 shown in FIG. 2 determines that the sensors are not in a steady state, method 200 continues to step 212. As described in further detail below, step 212 calculates a predictive temporal estimate for core body temperature and returns to step 206 to once again determine whether the sensors are in a steady state. According to steps 206 and 212, method 200 continues to calculate a predictive temporal estimate for core body temperature until a steady state of the sensors is achieved.

According to one embodiment of step 212, method 200 shown in FIG. 2 calculates a predictive temporal estimate for core body temperature according to Equation 1. In other words, Equation 1, shown below, provides an embodiment of the predictive temporal model of estimating body temperature when the sensors have not reached 'steady-state'.

$$T_{BodyTemp} = e^{-\left(\frac{\Delta t}{\tau}\right)} \times [\pm \alpha_1 T_{sensor1} \pm \alpha_2 T_{sensor2} \pm \alpha_3 (T_{sensor1} - T_{sensor2}) \pm \\ \alpha_4 (T_{sensor1} - T_{sensor2})^2 \pm \gamma] \quad (1)$$

As shown in FIG. 2, method 200 adaptively monitors the change in temperature sensor data (input received at steps 202 and 204) and predicts the body temperature during the transition phase (shown as a logic loop between steps 206 and 212). Although Equation 1 is shown above as utilizing an exponential, other embodiments are possible and include polynomial and logarithmic embodiments, for example.

According to embodiments described herein, the temperature sensors are determined to be in a "steady-state" (e.g., as shown in FIG. 2) by comparing the change in continuous temperature sensor readings to a standardized threshold in real-time. For example, the derivative (first or second) of the temperature readings from each of the sensors or the difference of the temperature readings can be calculated in real-time and compared against a pre-determined threshold. This pre-determined (standardized) threshold could be derived based on the thermal characteristics of the temperature sensors. When the temperature sensors (e.g., sensors 102*a* and 102*b* shown in FIG. 1) reach a steady-state, embodiments described herein estimate core body temperature based on the measurements of these sensors.

According to one embodiment described herein, method 200 shown in FIG. 2 is broadly described by Equation 2 below $$T_{BodyTemp} = \pm \sum_{i=1}^{N} [\alpha_i T_{sensor1}^N \pm \beta_i T_{sensor2}^N] \pm \sum_{i=1}^{N} \varepsilon_i (T_{sensor1} - T_{sensor2})^N \pm \\ \sum_{i=1}^{K} \delta_i \left(\frac{T_{sensor1}}{T_{sensor2}}\right)^K \pm \gamma \quad (2)$$

In Equation 1, τ→time-constant for the temperature sensors and Δt→time-elapsed. The coefficients ($\alpha_i$, $\beta_i$, $\varepsilon_i$, $\delta_i$, etc.) depend on age, gender, body-mass-index (BMI), ethnicity and physical health condition of the individual. Accordingly, these coefficients vary according to demographics. For example, the α-coefficients for an athlete would be completely different from the α-coefficients of an 80-year-old patient with arrhythmia. While not shown in FIG. 2, embodiments disclosed herein dynamically choose coefficients corresponding to demographics. From dynamically chosen coefficients, an embodiment of method 200 proceeds to estimate the core body temperature based on the steps shown in FIG. 2.

As previously mentioned, other embodiments of the claimed invention use all or some part of the model disclosed as Equation 2 above. For example, Equation 2 can be deconstructed into the following three equations:

$$T_{BodyTemp} = \pm \sum_{i=1}^{N} [\alpha_i T_{sensor1} \pm \beta_i T_{sensor2}] \quad (2A)$$

$$T_{BodyTemp} = \pm \sum_{i=1}^{N} [\alpha_i T_{sensor1} \pm \beta_i T_{sensor2}] \pm \sum_{i=1}^{N} \varepsilon_i (T_{sensor1} - T_{sensor2})^N \quad (2B)$$

$$T_{BodyTemp} = \quad (2C)$$
$$\pm \sum_{i=1}^{N} [\alpha_i T_{sensor1} \pm \beta_i T_{sensor2}] \pm \sum_{i=1}^{N} \varepsilon_i (T_{sensor1} - T_{sensor2})^N \pm$$
$$\sum_{i=1}^{K} \delta_i \left(\frac{T_{sensor1}}{T_{sensor2}}\right)^K$$

As shown above: Equation 2A is a simple linear model, Equation 2B compensates for heat loss, and Equation 2C models heat transfer between sensors. In other words, Equation 2A describes a linear model where the body temperature is calculated after combining two independent temperature sensors linearly using, as an example, the least square error method. Equation 2A is a simple and efficient calculation; however, by compensating for escaping heat, embodiments described herein improve the accuracy of our estimates. According to one embodiment, in Equation 2B, compensation of the heat loss is represented by the polynomial of the difference in the temperature sensors. Furthermore, by including the heat-transfer taking place between the temperature sensors, embodiments described herein further improve the accuracy of the estimates calculated by the embodiments shown by Equations 2A and 2B above. The heat-transfer between the two sensors is demonstrated by the division term as illustrated in Equation 2C.

As noted above, one benefit of the claimed invention is a simplification of the clinical workflow. Together, Equations 2, 2A, 2B and 2C provide a multitude of options readily apparent to one skilled in the art to use all or some part of the model used in method 200, shown in FIG. 2. For example, according to one embodiment, simplification of the clinical workflow is achieved by the incorporating a calibration term which calibrates real-time estimates derived from Equation 2 (as a whole) against a standardized clinical thermometer. In FIG. 2, this calibration is shown as step 210. In the model of Equation 2, the γ-term describes the correction factor resulting from this calibration.

FIG. 3 illustrates method 300 for core temperature monitoring in accordance with an embodiment. The method 300 includes providing a patch device, via step 302, coupling an electronic module to the patch device to provide a wearable device, via step 304, and monitoring health of a user using the wearable device, via step 306. In one embodiment, the patch device is disposable and the electronic module is reusable. In another embodiment, the patch device and electronic module are both disposable.

In one embodiment, the reusable electronic module is coupled by inserting the reusable electronic module into the core body temperature detection device that includes circuit connectors to receive the reusable electronic module. In such an embodiment, providing step 302 further comprises manufacturing and assembling the core body temperature detection device, where the patch device and electronic module are both disposable is some embodiments and not disposable in other embodiments.

As above described, a method and system in accordance with the present invention provide a wearable device that includes a disposable patch device component and a reusable or disposable electronic module component. The core temperature device component comprises a plurality of layers that house various components (e.g. a plurality of temperature sensors). The flexible and layered architecture of the disclosed core temperature device extends the usage and customizability of the device beyond what may be disclosed herein and can be manufactured at very high volumes and at very low costs. In addition, while not shown in the figures, the core temperature device is water resistance and can pass standards for water ingress such as IPX4 and IPX7.

In addition, by utilizing skin-friendly adhesives (for example, acrylic, silicone, hydrocolloid etc.) in the disclosed embodiments, the core temperature device is comfortably worn by the user with little or no skin irritation for long periods of time (e.g. no irritation for up to 7 days) and the removal stress is minimized to avoid damaging or discomforting the skin tissue. The flexibility of the core body temperature device maintains a high quality core body temperature measurement by being in contact with the user's body/skin with very low static noise and motion artifacts. Additionally, the core temperature device is unobtrusive and comfortable to a point that the user is unaware that it is attached to the body while the user is conducting active activities (e.g. walking, running), passive activities (e.g. watching television), and sleeping.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A system for core body temperature monitoring, the system comprising:
   a patch device; and
   an electronic module, coupled to the patch device, including a first sensor and a second sensor, wherein the electronic module:
   receives a first temperature measure from a first sensor,
   receives a second temperature from a second sensor,
   determines whether the first sensor and the second sensor are in a steady state by utilizing the first and second temperature,
   calculates a predictive temporal estimate in a logic loop according to an equation utilizing one of an exponential, polynomial, and logarithmic equation for core body temperature until the first sensor and the second sensor are in the steady state, and when the first sensor and the second sensor are in the steady state:
- if a reference device is available, receives a calibration correction factor calibrated to the reference device and calculates a core body temperature using the calibration correction factor, and
- if the reference device is not available, calculates a core body temperature using an adaptive correction factor.

2. The system of claim 1, wherein the patch device is disposable and the electronic module is at least one of a disposable module and a reusable module.

3. The system of claim 2, wherein the disposable patch device further comprises:
- a top layer;
- a sub-assembly layer coupled to the top layer; and
- a bottom layer coupled to the sub-assembly layer, wherein the top layer includes a first layer and a chamber area that resides on top of the first layer to house the electronic module.

4. The system of claim 3, wherein the first sensor and second sensor coupled to the patch device are coupled to the sub-assembly layer.

5. The system of claim 3, further comprising a plurality of spacers, wherein at least one spacer comprises an insulating material.

6. The system of claim 5, wherein the at least one spacer separates the first sensor and the second sensor.

7. The system of claim 5, wherein the at least one plurality of spacers includes any of closed cell foam, air, and polyethylene foam.

8. The system of claim 3, wherein the sub-assembly layer includes an electronic flex circuit.

9. The system of claim 8, wherein the electronic flex circuit includes at least two electrodes, a battery, and integrated connector circuits for the attachment of the electronic module.

10. The system of claim 3, wherein the bottom layer Includes an adhesive bottom layer.

11. The system of claim 1, further comprising at least one motion sensor to detect movement and adjust captured measurements of the first sensor and the second sensor according to the detected movements.

12. The system of claim 1, wherein the adaptive correction factor depends on at least one of: demographics, surround temperature range, or relative change in different temperature data-streams.

13. A method for detection core body temperature, the method performed by an electronic module configured for:
- receiving a first temperature measure from a first sensor;
- receiving a second temperature from a second sensor;
- determining whether the first sensor and the second sensor are in a steady state by utilizing the first and second temperature;
- calculating a predictive temporal estimate in a logic loop according to an equation utilizing one of an exponential, polynomial, and logarithmic equation for core body temperature until the first sensor and the second sensor are in the steady state; and
- when the first sensor and the second sensor are in the steady state:
  - if a reference device is available, receiving a calibration correction factor calibrated to the reference device and calculating a core body temperature using the calibration correction factor, and
  - if the reference device is not available, calculating a core body temperature using an adaptive correction factor.

14. The method of claim 13, wherein the determining whether the first sensor and the second sensor are in the steady state includes comparing changes in continuous temperature sensor measurements to a standardized threshold.

15. The method of claim 14, further comprising detecting movements and adjusting the calculated core body temperature according to the detected movements.

16. The method of claim 14, wherein the standardized threshold is based on the thermal characteristics of the first sensor and the second sensor.

17. The method of claim 13, further comprising a one-time calibration when initially calculating the core body temperature.

18. The method of claim 17, wherein the reference device includes a standardized clinical thermometer.

19. The method of claim 13, wherein the equation utilizing the exponential equation includes:

$$T_{BodyTemp} = e^{-\left(\frac{\Delta t}{\tau}\right)} \times [\pm \alpha_1 T_{sensor1} \pm \alpha_2 T_{sensor2} \pm \alpha_3 (T_{sensor1} - T_{sensor2}) \pm \alpha_4 (T_{sensor1} - T_{sensor2})^2 \pm \gamma],$$

wherein:
- $\tau$ corresponds to a time-constant for the temperature sensors $T_{sensor}$,
- $\Delta t$ corresponds to a time-elapsed,
- $\alpha_i$ corresponds to a coefficient depending on at least one of: age, gender, body-mass-index (BMI), ethnicity or physical health condition of an individual, and
- $\gamma$ corresponds to a correction factor.

20. A method for core body temperature monitoring, the method comprising:
- providing a patch device;
- coupling an electronic module to the patch device to provide a wearable device, the electronic module including at least two temperature sensors; and
- monitoring core body temperature of a user using the wearable device by:
  - receiving a first temperature measure from a first sensor of the at last two temperature sensors,
  - receiving a second temperature from a second sensor of the at last two temperature sensors,
  - determining whether the first sensor and the second sensor are in a steady state by utilizing the first and second temperature,
  - calculating a predictive temporal estimate in a logic loop according to an equation utilizing one of an exponential, polynomial, or logarithmic equation for core body temperature until the first sensor and the second sensor are in the steady state, and
  - when the first sensor and the second sensor are in the steady state:
    - if a reference device is available, receiving a calibration correction factor calibrated to the reference device and calculating a core body temperature using the calibration correction factor, and
    - if the reference device is not available, calculating a core body temperature using an adaptive correction factor.

* * * * *